United States Patent
Liang et al.

(10) Patent No.: US 10,192,642 B2
(45) Date of Patent: Jan. 29, 2019

(54) SYSTEM AND METHOD FOR DETERMINING AN ASSOCIATION OF AT LEAST ONE BIOLOGICAL FEATURE WITH A MEDICAL CONDITION

(71) Applicant: Macau University of Science and Technology, Taipa (MO)

(72) Inventors: Yong Liang, Taipa (MO); Hua Chai, Taipa (MO); Xiao-Ying Liu, Taipa (MO)

(73) Assignee: MACAU UNIVERSITY OF SCIENCE AND TECHNOLOGY, Taipa (MO)

( * ) Notice: Subject to any disclaimer, the term of this patent is extended or adjusted under 35 U.S.C. 154(b) by 109 days.

(21) Appl. No.: 15/150,639

(22) Filed: May 10, 2016

(65) Prior Publication Data
US 2017/0329926 A1 Nov. 16, 2017

(51) Int. Cl.
*G06F 19/00* (2018.01)
*G06F 19/12* (2011.01)
*G16H 50/50* (2018.01)

(52) U.S. Cl.
CPC .......... *G16H 50/50* (2018.01); *G06F 19/00* (2013.01); *G06F 19/12* (2013.01)

(58) Field of Classification Search
CPC .............................. G06F 19/345; G06N 7/005
See application file for complete search history.

(56) References Cited

U.S. PATENT DOCUMENTS

| | | | |
|---|---|---|---|
| 2013/0144584 A1* | 6/2013 | Chen | G06F 19/3456 703/11 |
| 2015/0218649 A1* | 8/2015 | Saenger | C12Q 1/6886 424/85.2 |
| 2015/0220838 A1* | 8/2015 | Martin | G06F 19/12 706/12 |
| 2017/0097347 A1* | 4/2017 | Eastman | G01N 33/564 |

OTHER PUBLICATIONS

D. W. Hosmer, Jr. et al., "Applied Logistic Regression", John Wiley & Sons, 2004, pp. 313-456.
Jelle J. Goeman, "L1 Penalized Estimation in the Cox Proportional Hazards Model", Biometrical Journal, 2010, vol. 52, No. 1, pp. 70-84.
J. Li et al., "A Novel Approach to Feature Extraction from Classification Models Based on Information Gene Pairs", Pattern Recognition, 2008, vol. 41, No. 6, pp. 1975-1984.
(Continued)

*Primary Examiner* — Changhyun Yi
(74) *Attorney, Agent, or Firm* — Renner Kenner Greive Bobak Taylor & Weber

(57) ABSTRACT

A system and a method for determining an association of at least one biological feature with a medical condition, in particularly, but not exclusively, a system and a method of determining an association of at least one biological feature in form of a gene expression with cancer or a subtype of cancer that can include the generation of a simplified protein-protein interaction network based on processed biological data. The system and respective method is especially suitable for analysis of high dimensional and low sample size biological datasets such as in cancer research.

9 Claims, 10 Drawing Sheets

(56) References Cited

OTHER PUBLICATIONS

X-J. MA et al., "A Two-Gene Expression Ratio Predicts Clinical Outcome in Breast Cancer Patients Treated with Tamoxifen", Cancer Cell, 2004, vol. 5, No. 6, pp. 607-616.

J. A. K. Suykens et al., "Least Squares Support Vector Machine Classifiers", Neural Processing Letters, 1999, vol. 9, No. 3, pp. 293-300.

A. E. Hoerl et al., "Ridge Regression: Biased Estimation for Nonorthogonal Problems", Technometrics, 2000, vol. 42, No. 1, pp. 79-86.

J. Zhu et al., "1-norm Support Vector Machines", Advances in Neural Information Processing Systems, 2004, vol. 16, No. 1, pp. 49-56.

E. Bair et al., "Semi-Supervised Methods to Predict Patient Survival from Gene Expression Data", PLoSBiol, 2004, vol. 2, No. 4, E108, pp. 0511-0522.

C. Li et al., "Network-Constrained Regularlization and Variable Selection for Analysis of Genomic Data", Bioinformatics (2008), vol. 24., No. 9, pp. 1175-1182.

W. Zhang et al., "Network-Based Survival Analysis Reveals Subnetwork Signatures for Predicting Outcomes of Ovarian Cancer Treatment", PLoSComputBiol, (2013), vol. 9, No. 3, e1002975, pp. 1-16.

C. Han et al., "Networkk-Based Classification of Breast Cancer Metastasis", Molecular Systems Biology, 2007, vol. 3, No. 1, 140, pp. 1-10.

C. Brouard et al., "Regularized Output Kernel Regression Applied to Protein-Protein Interaction Network Inference", NIPS MLCG Workshop, 2010, pp. 1-6.

W. Zhang et al., "Molecular Pathway Identification Using Biological Network-Regularized Logistic Models", BMC Genomics, 2013, 14. Supp. 8, S7, pp. 1-8.

X. Zongben et al., "L 1/2 Regularization: A Thresholding Representation Theory and a Fast Solver", IEEE Transactions on Neural networks and Learning Systems, 2012, vol. 23, No. 7, pp. 1013-1027.

Y. Liang et al., "Sparse Logistic Regression with a L 1/2 Penalty for Gene Selection in Cancer Classification", BMC Bioinformatics, 2013, vol. 14, No. 1, pp. 1-12.

C. Liu et al., The L 1/2 Regularization Method for Variable Selection in the Cox Model, Applied Soft Computing, 2014, vol. 14, pp. 498-503.

H. Chai et al., "The L 1/2 Regularization Approach for Survival Analysis in the Accelerated Failure Time Model", Computers in Biology and Medicine, 2015, vol. 64, pp. 283-290.

C. Stark et al., "BioGRID: A General Repository for Interaction Datasets", Nucleic Acids Research, 2006, vol. 34, Suppl. 1, pp. D535-D539.

F. R. K. Chung, "Spectral Graph Theory", Conference Board of the Mathematical Sciences (CBMS), Regional Conference Series in Mathematics, No. 92, 1997, pp. 123-131.

H. Zou et al., "Regularization and Variable Selection via the Elastic Net", Journal of the Royal Statistical Society: Series B (Statistical Methodology), 2005, vol. 67, No. 2, pp. 301-320.

Z. Xu et al., "L 1/2 Regularization", Science China Information Sciences, 2010, vol. 53, No. 6, pp. 1159-1169.

X-L Wu et al., "Osteopontin Knockdown Suppresses the Growth and Angiogenesis of Colon Cancer Cells", World Journal of Gastroenterology: WJG, 2014, vol. 20, No. 30, pp. 10440-10449.

Y. Lin et al., "Inorganic Phosphate Induces Cancer Cell Mediated Angiogenesis Dependent on Forkhead Box Protein C2 (FOXC2) Regulated Osteopontin Expression", Molecular Carcinogenesis, 2014, pp. 1-9.

B. Patel et al., "Aberrant TAL1 Activation is Mediated by an Interchromosomal Interaction in Human T-Cell Acute Lymphoblastic Leukemia", Leukemia, 2014, vol. 28, No. 2, pp. 349-361.

M. Loosveld et al., "MYC Fails to Efficiently Shape Malignant Transformation in T-Cell Acute Lymphoblastic Leukemia", Genes, Chromosomes and Cancer, 2014, vol. 53, No. 1, pp. 52-66.

S. Sayhan et al., "Expression of Caveolin-1 in Peritumoral Stroma is Associated with Histological Grade in Ovarian Serous Tumors", Ginekologiapolska, 2015, vol. 86, No. 6, pp. 424-428.

Z. Zhao et al., "Loss of Stromal Caveolin-1 Expression in Colorectal Cancer Predicts Poor Survival", World Journal of Gastroenterology, WJG, 2015, vol. 21, No. 4, pp. 1140-1147.

M. Martini et al., "The Candidate Tumor Suppressor SASH1 Interacts with the Actin Cytoskeleton and Stimulates Cell-Matrix Adhesion", The International Journal of Biochemistry & Cell Biology, 2011, vol. 43, No. 11, pp. 1630-1640.

Y. Shen et al., "The Catalase C-262T Gene Polymorphism and Cancer Risk: A Systematic Review and Meta-Analysis", Medicine, 2015, vol. 94, No. 13, e679, pp. 1-8.

H. Qin et al., "Elevated Expression of CRYAB Predicts Unfavorable Prognosis in Non-Small Cell Lung Cancer", Medical Oncology, 2014, vol. 31, No. 8, pp. 1-8.

S. Banerjee et al., "Regulation of the Metastasis Suppressor Nm23-H1 by Tumor Viruses", Naunyn-Schmiedeberg's Archives of Pharmacology, 2014, vol. 388, No. 2, pp. 207-224.

N. Niitsu, "The Association of Nm23-H1 Expression with a Poor Prognosis in Patients with Peripheral T-Cell Lymphoma, Not Otherwise Specified", Journal of Clinical and Experimental Hematopathology, 2014, vol. 54, No. 3, pp. 171-177.

S. Dinesh et al., "Gene Expression Correlates of Clinical Prostate Cancer Behavior", Cancer Cell, 2002, vol. 1, No. 2, pp. 203-209.

M. T. Landi et al., "Gene Expression Signature of Cigarette Smoking and its Role in Lung Adenocarcinoma Development and Survival", PLoS one, 2008, vol. 3, No. 2, e1651, pp. 1-8.

* cited by examiner

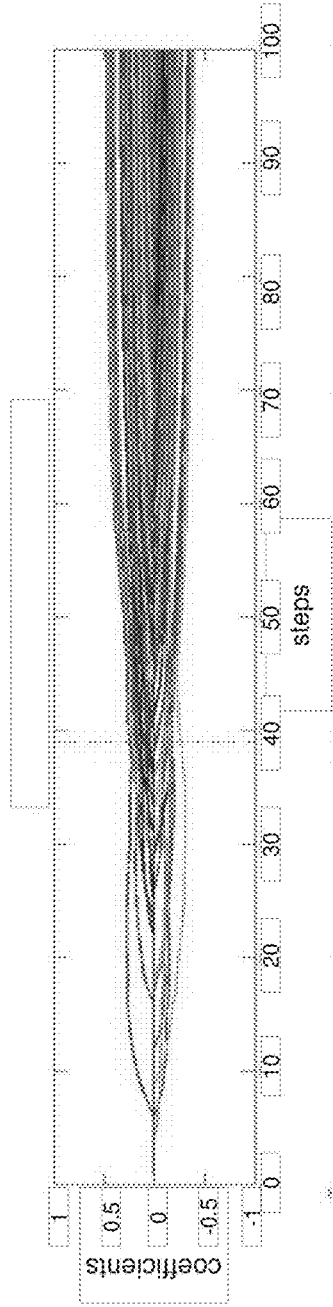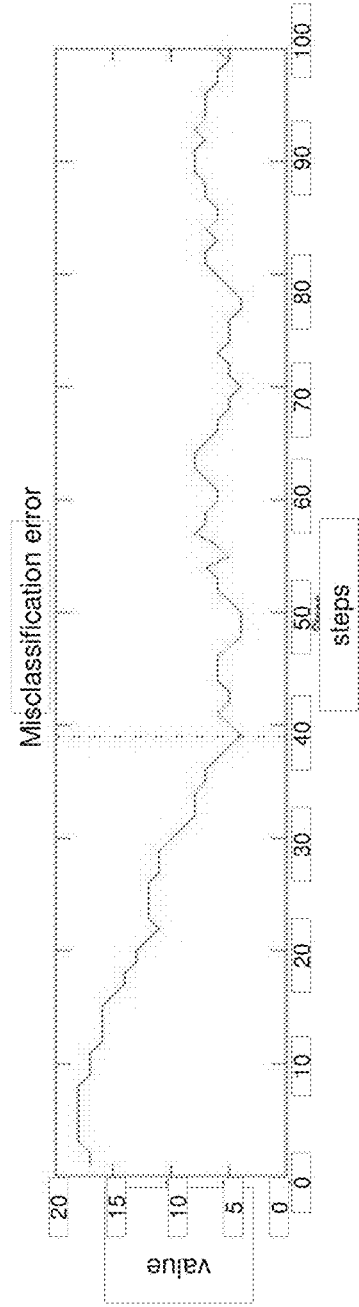
FIG. 3A
FIG. 3B
FIG. 3

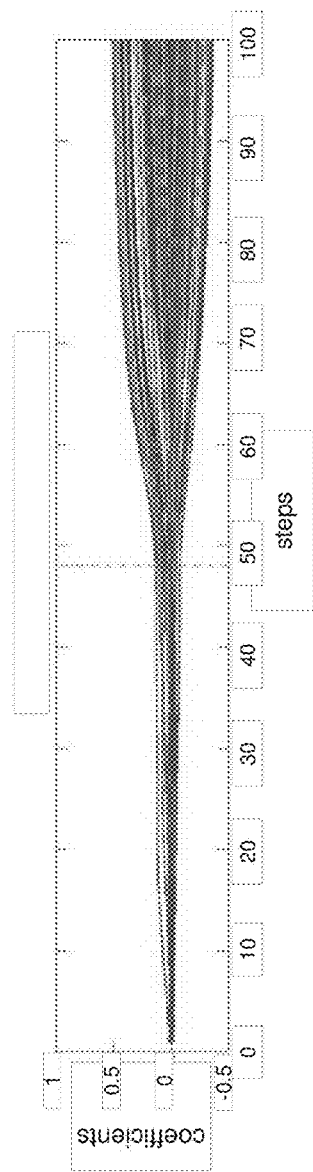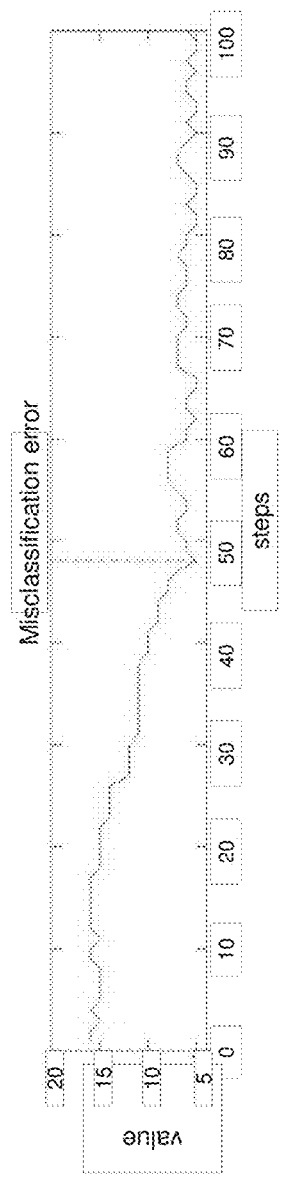
FIG. 4A    FIG. 4B
FIG. 4

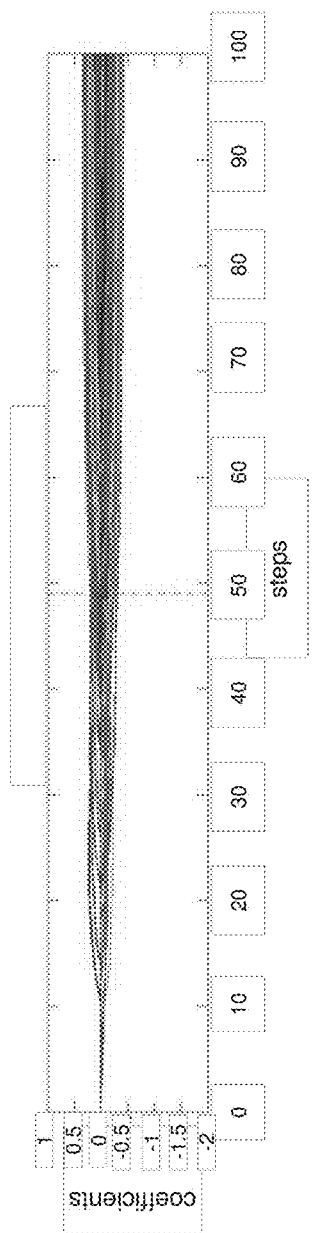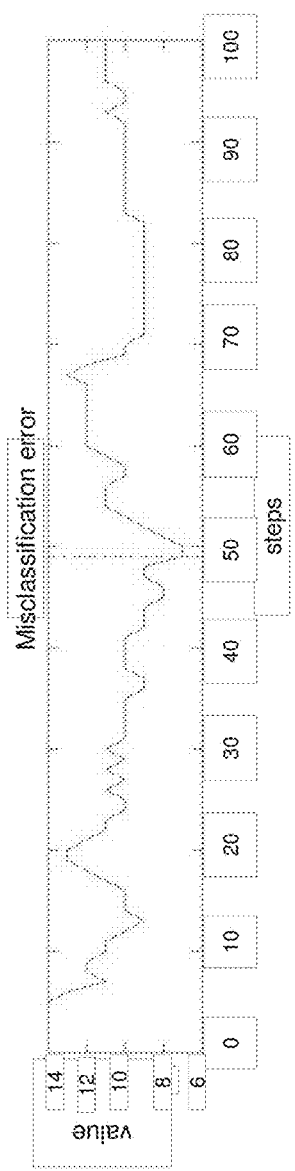
FIG. 5A
FIG. 5B
FIG. 5

SYSTEM AND METHOD FOR DETERMINING AN ASSOCIATION OF AT LEAST ONE BIOLOGICAL FEATURE WITH A MEDICAL CONDITION

TECHNICAL FIELD

The present invention relates to a system and a method for determining an association of at least one biological feature with a medical condition, in particularly, but not exclusively, to a system and a method for determining an association of at least one biological feature in form of a gene expression with cancer or a subtype of cancer which can include the generation of a simplified protein-protein interaction network.

BACKGROUND

How to classify the patients and select the related genes as a promising approach for diagnosis and treatment selection represents a challenge. In particular, selecting biomarker genes and finding the interaction pathways with high-dimensional and low-sample size microarray data is a big challenge in the computational biology. In this field, inference of protein-protein interaction (PPI) networks using the selected genes for diseases has attracted attention of many researchers. The support vector machine (SVM) is commonly used to classify the patients and a number of useful tools such as Lasso, Elastic net, SCAD or some other regularized methods which were combined with the SVM model to select the feature genes which are related to a disease.

There, however, remains a strong need for systems and associated methods for determining an association of biological features like gene expression with a medical conditions which are effective and ensure sufficient accuracy of the prediction even in case of high-dimensional and low-sample size microarray data. Clearly, having a respective system and method could significantly contribute to an improved diagnosis and treatment selection such as for diseases like cancer.

SUMMARY OF THE INVENTION

In accordance with a first aspect of the present invention, there is provided a method of determining an association of at least one biological feature with a medical condition, comprising the steps of:

obtaining a dataset comprising biological data related to a plurality of samples each having a plurality of biological features;

applying at least some of the biological data to a regression model to determine and/or optimize parameters in the regression model thereby solving the regression model;

processing the biological data using the solved regression model with a biological model to determine one or more biological features that are associated with the medical condition.

"Samples" as used herein can be derived from at least one animal or human, in particular from at least one mammal. Preferably but not exclusively, the samples are derived from at least one human. The samples are in particular of cancerous tissue derived from at least one human. In an embodiment, the samples can be of cancerous tissue derived from a human.

The "biological data" include a plurality of biological features. A biological feature can be selected from, for example, gene expression, i.e. gene expression level, presence of a gene, presence of a gene product or amount of a gene product. A gene product is usually a protein or peptide encoded by the gene including a mutated form of the gene.

The expression "association of at least one biological feature with a medical condition" generally means any kind of expected link or connection between both, in an embodiment "association" means that the medical condition is or is expected to be caused by the at least one biological feature, the at least one biological feature at least contribute to the medical condition or its clinical worsening, and/or the at least one biological feature is involved in cellular processes which cause or contribute or are expected to cause or contribute to the medical condition or its clinical worsening.

The medical condition is in particular a disease like cancer or a subtype of cancer.

In an embodiment, the regression model includes a support vector machine model with a network constraint.

In an embodiment, in particular in the afore-mentioned embodiment, the regression model includes $L_{1/2}$ regularization.

The biological model can be generated with the present method or can be a preexisting biological model, in particular it can include protein-protein-network information.

In an embodiment, the method further comprises the step of generating or obtaining the biological model for determining the association between the one or more biological features and the medical condition.

In an embodiment, the biological model includes protein-protein interaction network information associated with the one or more biological features and the medical condition. In this embodiment, the step of processing the biological data using the solved regression model with a biological model comprises the step of constructing a Laplacian matrix representing the dataset and/or the protein-protein interaction network information. The step of processing the biological data using the solved regression model with a biological model can further comprise the step of introducing a network constraint to the model based on the Laplacian matrix.

In an embodiment, in particular in an afore-mentioned embodiment, the step of processing the biological data using the solved regression model with a biological model includes an iterative transformation for obtaining at least one estimation representing correlation between the one or more biological features and the medical condition. In this embodiment, the iterative transformation can include a soft thresholding operation of a coordinate descent optimization of the regularized protein-protein interaction network information for obtaining the model. In this embodiment, a thresholding representation of $$\frac{\sqrt[3]{54}}{4}(\lambda)^{\frac{2}{3}}$$

can be used in the soft thresholding operation, wherein $\lambda$ denotes a regularization parameter.

In an embodiment, the at least one biological feature includes at least one of presence of a gene, gene expression, presence of a gene product or amount of a gene product, and the medical condition is cancer. In this embodiment, the at least one biological feature associated with the medical condition is at least one biomarker and/or indicator arranged to represent an indication of the medical condition.

In a particular embodiment, the at least one biomarker and/or indicator is at least one gene expression, i.e. gene expression level(s).

The term "biomarker" as used herein in particular means biological features like presence of genes, gene expression, presence of gene products or amount of gene products that are indicative of the medical condition, i.e. represent an indication of the medical condition, like cancer. "Indicative of the medical condition" or "represent an indication of the medical condition" as expressions used herein means that the at least one biological feature is found at all or is found significantly more often in subjects with the medical condition than in healthy subjects or in subjects suffering from another medical condition and is in particular associated with the medical condition, i.e. there is a link or connection between the biological feature and the medical condition or such link or connection is assumed.

Preferably but not exclusively, the at least one biological feature is expression of at least one gene, i.e. gene expression level, and the medical condition is cancer or a subtype of cancer.

In accordance with a second aspect of the present invention, there is provided a system for determining an association of at least one biological feature with a medical condition, comprising a processing module arranged to:

apply at least some of the biological data in a dataset comprising biological data related to a plurality of samples each having a plurality of biological features to a regression model so as to determine and/or optimize parameters in the regression model thereby solving the regression model; and process the biological data using the solved regression model with a biological model to determine one or more biological features that are associated with the medical condition.

In an embodiment of the system of the present invention, the model includes a support vector machine model with a network constraint.

In an embodiment of the system of the present invention, in particular in the afore-mentioned embodiment, the model includes $L_{1/2}$ regularization.

The biological model can be generated with the present method or can be a preexisting biological model, in particular it can include protein-protein-network information.

In an embodiment of the system of the present invention, the biological model is generated by the processing module or is obtained from a database.

In an embodiment of the system of the present invention, the biological model includes protein-protein interaction network information associated with the one or more biological features and the medical condition.

In an embodiment of the system of the present invention, in particular in the afore-mentioned embodiment, the processing module is further arranged to construct a Laplacian matrix representing the dataset and/or the protein-protein interaction network information. The transformation module can in this embodiment be arranged to perform an iterative transformation for obtaining at least one estimation representing correlation between the one or more biological features and the medical condition.

In an embodiment of the system of the present invention, the at least one biological feature includes at least one of presence of a gene, gene expression, presence of a gene product or amount of a gene product, and the medical condition is cancer. In particular, the at least one biological feature refers to at least one gene expression, i.e. gene expression level.

Other features and aspects of the invention will become apparent by consideration of the following detailed description and accompanying drawings.

BRIEF DESCRIPTION OF THE DRAWINGS

FIG. 3A and 3B show the coefficient paths and misclassification errors obtained by a Net-SVM with $L_{1/2}$ regularization model of the present invention in the simulation experiment. The vertical dotted line was drawn at the optimal solution which is determined by the value of the minimal misclassification computed by the 10-fold cross validation.

FIG. 4A and 4B show the coefficient paths and misclassification errors obtained by Net-SVM with SCAD in the simulation experiment. The vertical dotted line was drawn at the optimal solution which is determined by the value of the minimal misclassification computed by the 10-fold cross validation.

FIG. 5A and 5B show the coefficient paths and misclassification errors obtained by Net-SVM with Lasso in the simulation experiment. The vertical dotted line was drawn at the optimal solution which is determined by the value of the minimal misclassification computed by the 10-fold cross validation.

DETAILED DESCRIPTION OF THE INVENTION

Figure 1:
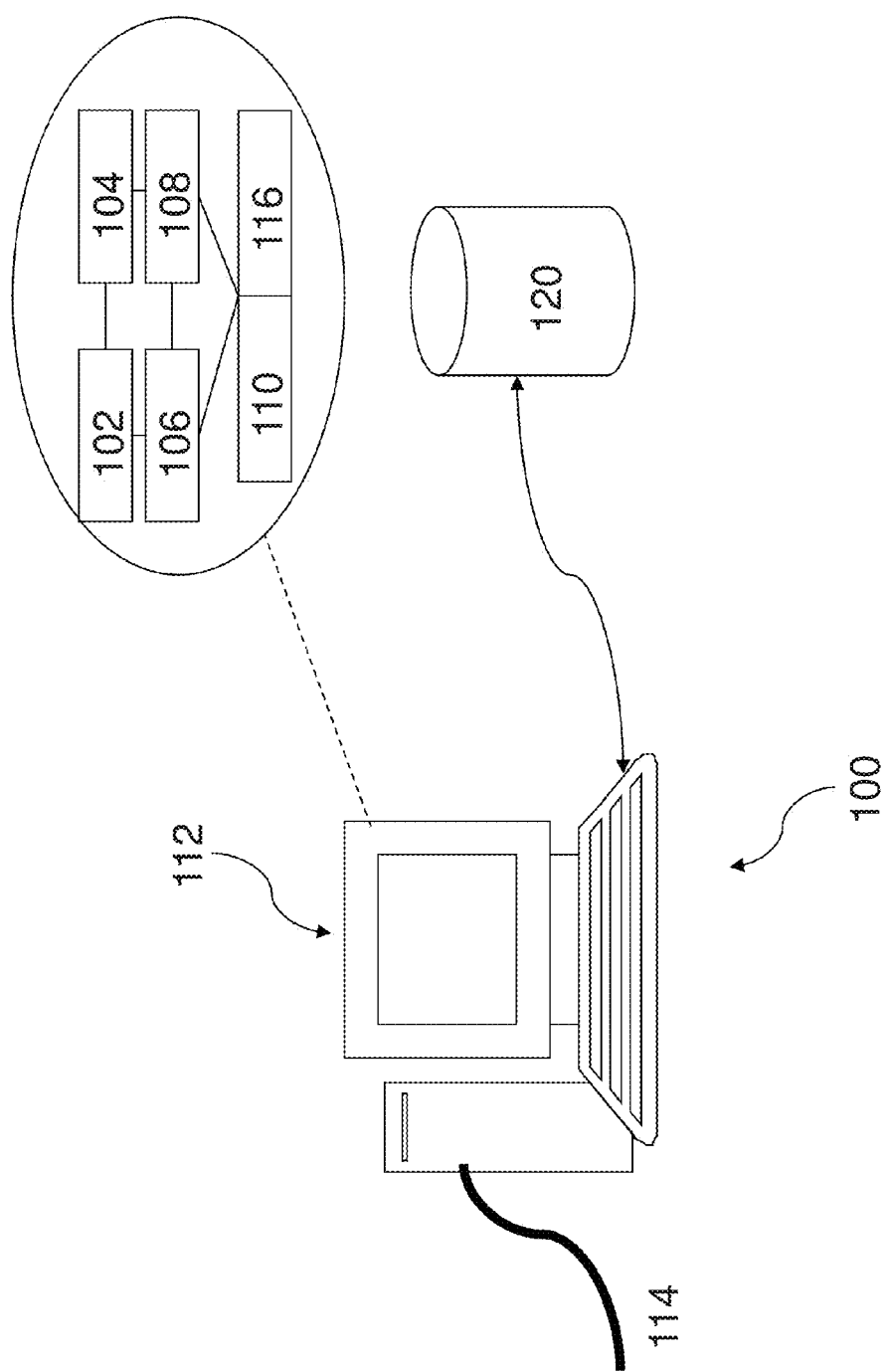
FIG. 1 is a schematic diagram of a computer or computing server arranged to operate a system of the present invention for determining an association of at least one biological feature with a medical condition.

The inventors based on their research, tests and experiments concluded that the support vector machine (SVM) (Suykens, Johan A K, and Joos Vandewalle, Neural processing letters 9.3 (1999): 293-300) with different regularization methods can be applied in the disease classification and feature selection. Due to the high dimensional and low sample size microarray gene data, the SVM model is usually regularized with penalties such as $L_2$-norm or $L_1$-norm Lasso regularization (Hoerl, Arthur E., and Robert W. Kennard, Technometrics 12.1 (1970): 55-67, Zhu, Ji, et al., Advances in neural information processing systems 16.1 (2004): 49-56) and so on. The advantages of the regularization method are to achieve a minimization of the regression errors and to select the relevant variables simultaneously through generating sparse solutions.

The SVM model has been shown great success in outcome prediction for different kinds of cancers. However, the inventors herein concluded that a weakness of SVM is that it may not consider the biologically meaning in cancer treatment (Bair, Eric, and Robert Tibshirani, PLoSBiol 2.4 (2004): E108). To overcome this drawback, Li et al. (Bioinformatics 24.9 (2008): 1175-1182) proposed a simple and fast network-constrained regularization procedure which can identify related genes and build network which was relevant to the disease or disease outcome. Recently, many similar methods have been proposed using the gene expression data to construct a protein-protein interaction (PPI) network based on the some other supervised learning methods such as logistic regression model or Cox model, which were combined with different regularization methods (Zhang, Wei, et al., PLoSComputBiol 9.3 (2013): e1002975, Chuang, Han-Yu, et al., Molecular systems biology 3.1 (2007): 140, Brouard, Céline, et al., Regularized output kernel regression applied to protein-protein interaction network inference, NIPS MLCB Workshop. 2010, Zhang, Wen, et al., BMC genomics 14.Suppl 8 (2013): S7).

Generally, the widely used $L_2$-norm or the $L_1$-norm regularization methods may select a large number of irrelevant disease genes, which significantly increases the research costs, and make the constructed network more complex. Xu et al. (L1/2 regularization: a thresholding representation theory and a fast solver, IEEE Transactions on neural networks and learning systems 23.7 (2012): 1013-1027) proposed the $L_{1/2}$ regularization method to find the more sparse solution. The inventors herein found that the $L_{1/2}$ regularization has good statistic properties, such as sparsity, unbiasedness, and oracle properties, and has been successfully applied to some real data analyzes (Liang, Yong, et al., BMC bioinformatics 14.1 (2013): 198, Liu, Cheng, et al., Applied Soft Computing 14 (2014): 498-503, Chai, Hua, et al., The L1/2 regularization approach for survival analysis in the accelerated failure time model, Computers in biology and medicine (2014)).

The inventors further found that the $L_{1/2}$ regularization was, however, only used for gene selection (Bair, Eric, and Robert Tibshirani, PLoSBiol 2.4 (2004): E108).

In order to get a more accurate, and in order to get a biologically meaningful result at all, the inventors herein combined the network-constrained procedure and the $L_{1/2}$ regularization and discovered a new Net-SVM model.

Without being bound by theory, the inventors herein through their research, tests and experiments discovered that in particular a Net-SVM model with $L_{1/2}$-norm regularization can be used in a regression model for cancer classification, gene selection and protein-protein interaction network construction.

In this embodiment, the system for determining an association of at least one biological feature with a medical condition is implemented by or for operation on a computer having an appropriate user interface. The computer may be implemented by any computing architecture, including stand-alone PC, client/server architecture, "dumb" terminal/mainframe architecture, or any other appropriate architecture. The computing device is appropriately programmed to implement the invention.

Referring to FIG. 1, there is a shown a schematic diagram of a computer or a computing server 100 which in this embodiment comprises a server 100 arranged to operate, at least in part if not entirely, the system for determining an association of at least one biological feature with a medical condition in accordance with one embodiment of the present invention. The server 100 comprises suitable components necessary to receive, store and execute appropriate computer instructions. The components may include a processing unit 102, read-only memory (ROM) 104, random access memory (RAM) 106, and input/output devices such as disk drives 108, input devices 110 such as an Ethernet port, a USB port, etc., display 112 such as a liquid crystal display, a light emitting display or any other suitable display and communications links 114. The server 100 includes instructions that may be included in ROM 104, RAM 106 or disk drives 108 and may be executed by the processing unit 102. There may be provided a plurality of communication links 114 which may variously connect to one or more computing devices such as a server, personal computers, terminals, wireless or handheld computing devices. At least one of a plurality of communications link may be connected to an external computing network through a telephone line or other type of communications link.

The server 100 may include storage devices such as a disk drive 108 which may encompass solid state drives, hard disk drives, optical drives or magnetic tape drives. The server 100 may use a single disk drive or multiple disk drives. The server 100 may also have a suitable operating system 116 which resides on the disk drive or in the ROM of the server 100.

The system has a database 120 residing on a disk or other storage device which is arranged to store a dataset. The database 120 is in communication with the server 100 with an interface, which is implemented by computer software residing on the server 100. Alternatively, the database 120 may also be implemented as a stand-alone database system in communication with the server 100 via an external computing network, or other types of communication links.

Figure 2:
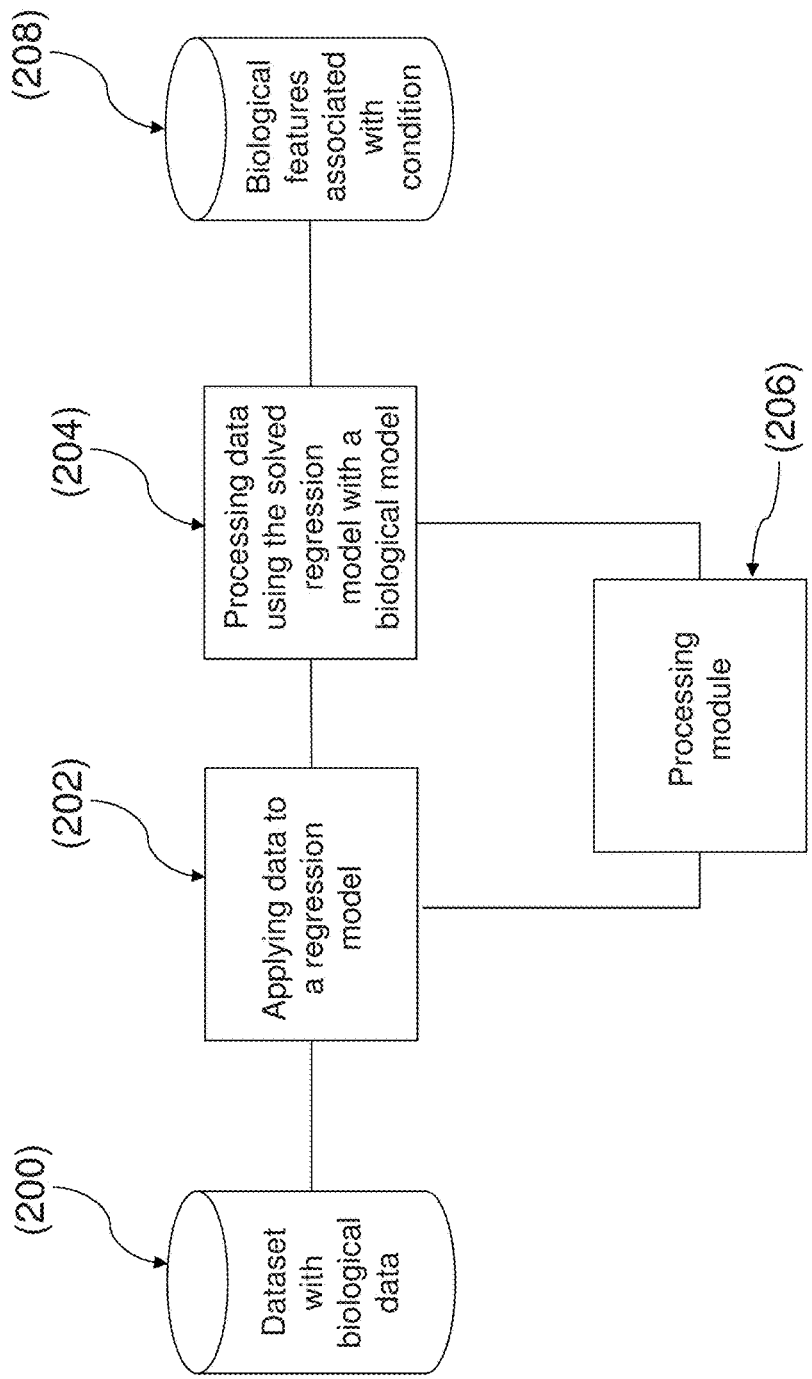
FIG. 2 is a schematic diagram showing a system of the present invention for determining an association of at least one biological feature with a medical condition.
Figure 6:
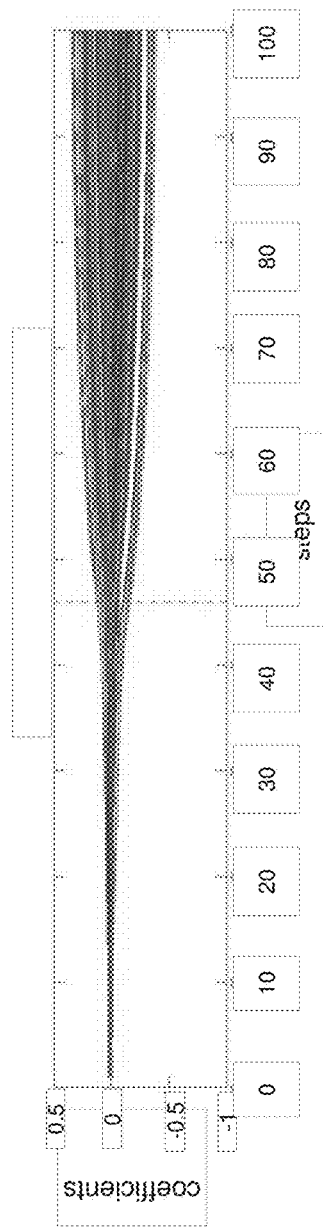
FIG. 6A and 6B show the coefficient paths and misclassification errors obtained by Net-SVM with elastic net in the simulation experiment. The vertical dotted line was drawn at the optimal solution which is determined by the value of the minimal misclassification computed by the 10-fold cross validation.
Figure 6:
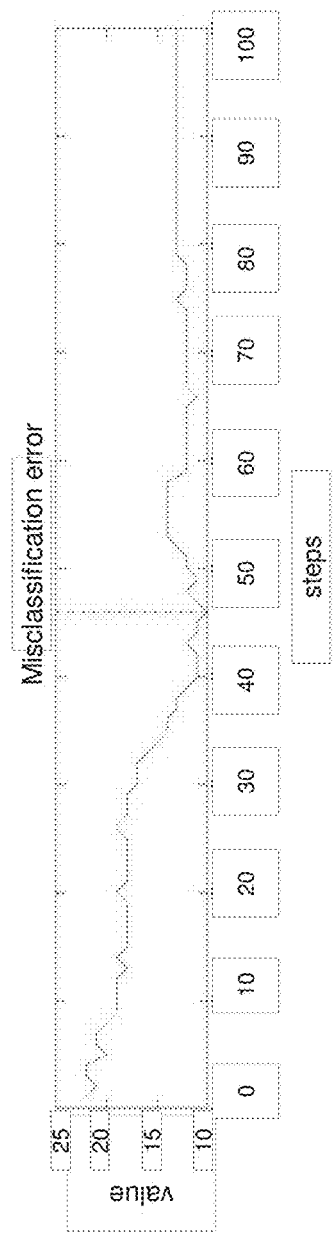
Figure 7:
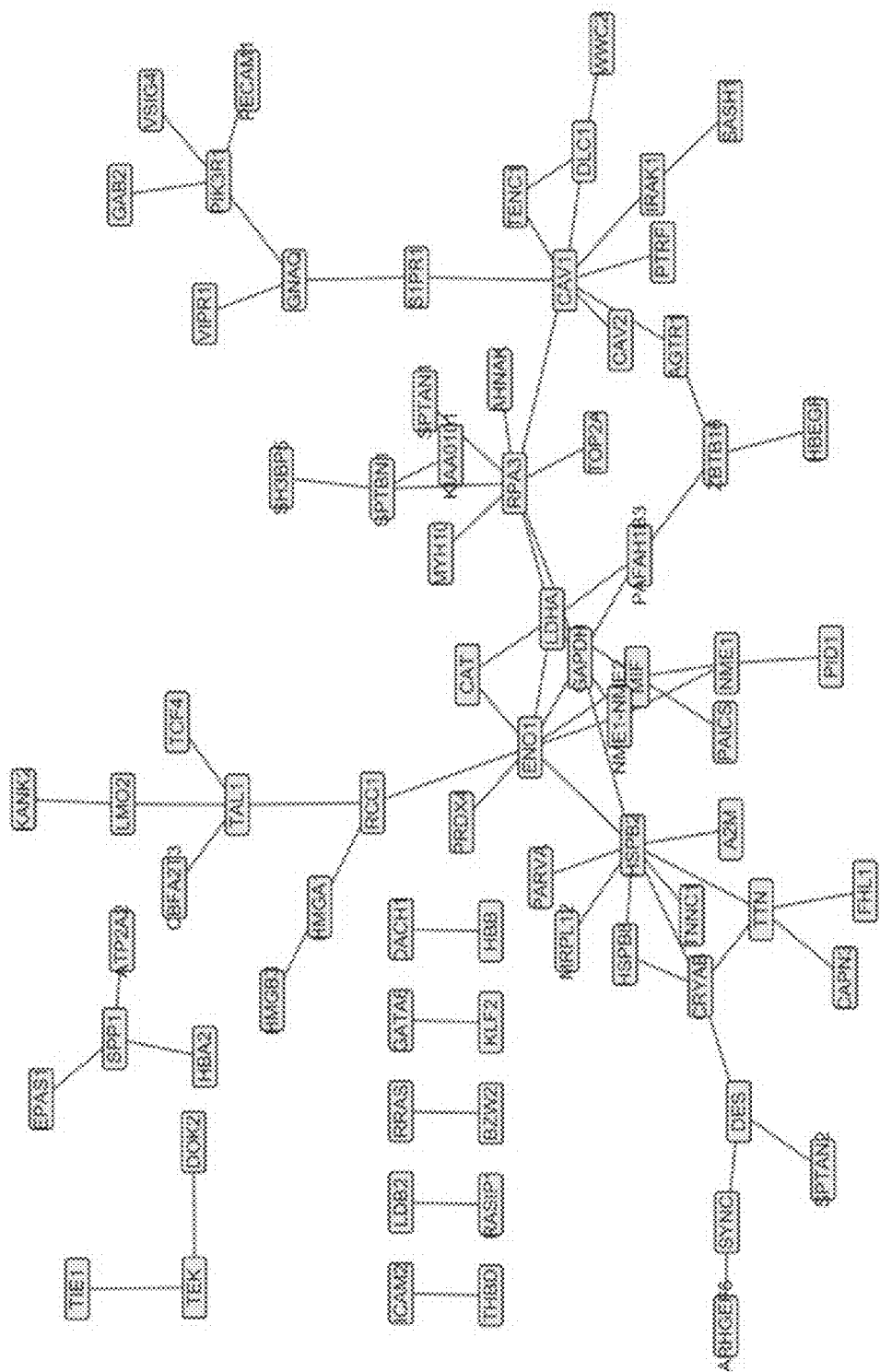
FIG. 7 illustrates the PPI network for lung cancer obtained by a $L_{1/2}$ penalized Net-SVM regression model of the present invention.
Figure 8:
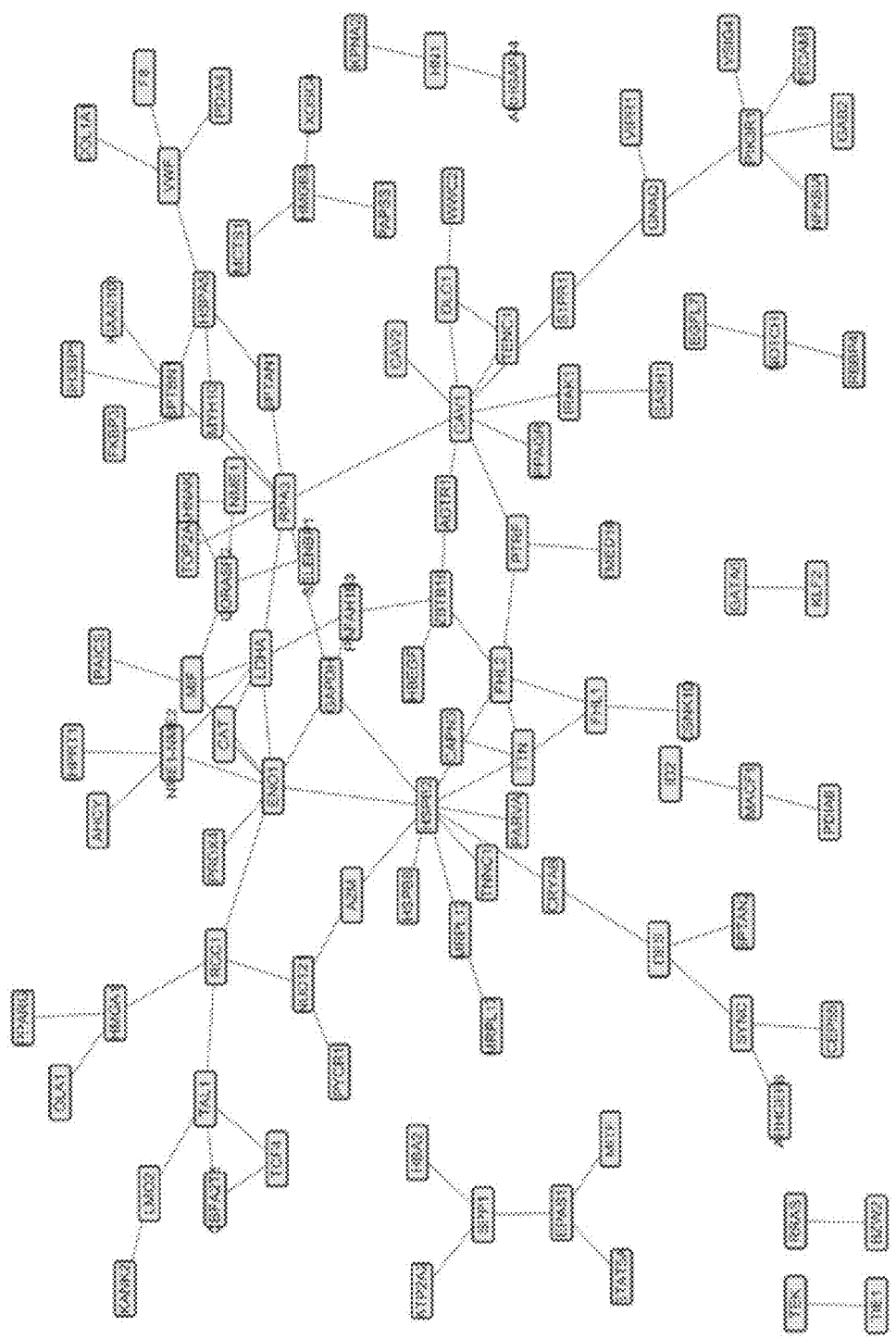
FIG. 8 illustrates the PPI network for lung cancer obtained by SCAD penalized Net-SVM.
Figure 9:
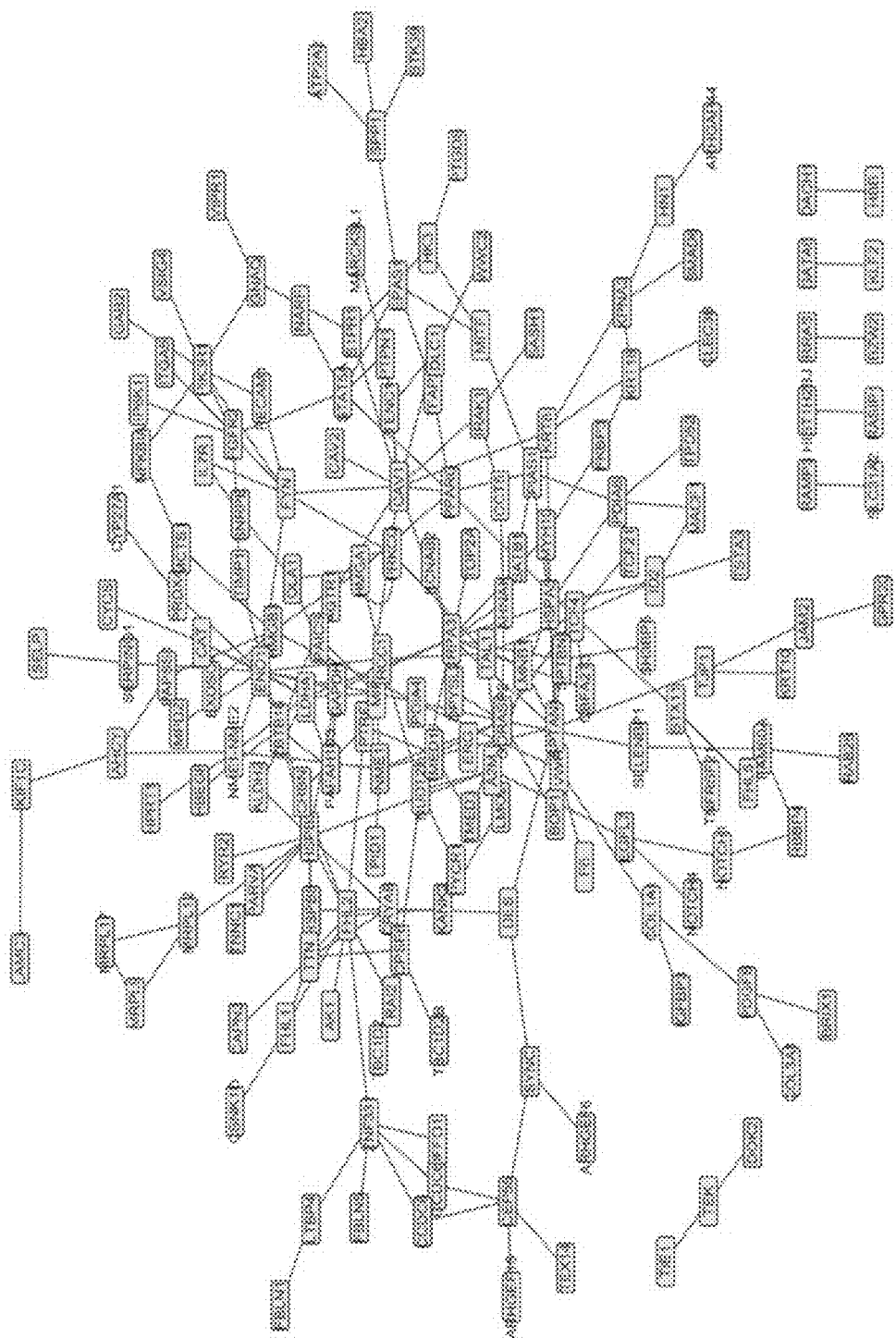
FIG. 9 illustrates the PPI network for lung cancer obtained by Lasso penalized Net-SVM.
Figure 10:
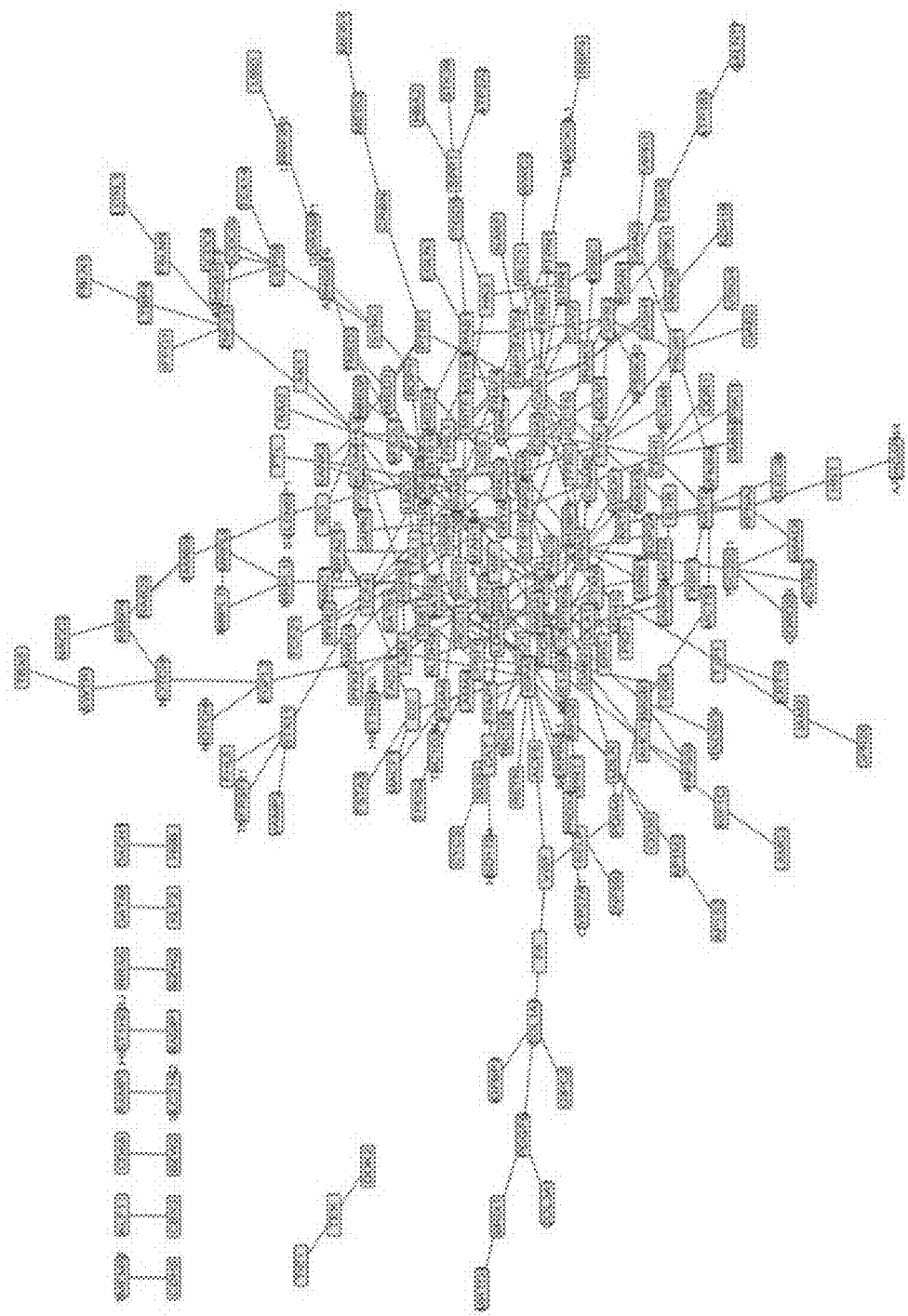
FIG. 10 illustrates the PPI network for lung cancer obtained by elastic net penalized Net-SVM.

With reference to FIG. 2, there is provided a system for determining an association of at least one biological feature with a medical condition, comprising a processing module 206 arranged to:

apply at least some of the biological data in a dataset 200 comprising biological data related to a plurality of samples each having a plurality of biological features to a regression model (202) so as to determine and/or optimize parameters in the regression model thereby solving the regression model; and process the biological data using the solved regression model with a biological model (204) to determine one or more biological features 208 that are associated with the medical condition.

In this embodiment, the system may include a processing module 206 arranged to apply at least some of the biological data in a dataset 200 comprising biological data related to a plurality of samples from humans each having a plurality of biological features including gene expression to a regression model (202) so as to determine and/or optimize parameters in the regression model thereby solving the regression model, wherein the model includes a Net-SVM model with $L_{1/2}$ regularization. This model can be completed by the coordinate descent method with the Newton-Raphson iterative method.

The processing module is further arranged in this embodiment to process the biological data using the solved regression model with a biological model (204) including protein-protein-network information to determine one or more biological features 208 being one or more gene expression that are associated with a medical condition such as cancer.

These processes, which can include methods of the present invention, may be implemented as a plurality of steps on a computer or computing device, such as those as found in FIG. 1.

The system of the present invention utilizing in an embodiment a novel Net-SVM model with $L_{1/2}$ regularization is especially suitable and highly advantageous for selecting significantly relevant biomarkers in high dimensional and low sample size biological datasets and can include construction of a protein-protein interaction network for a disease like cancer.

Experimental results confirmed that the Net-SVM model with $L_{1/2}$ regularization utilized by the system of the present invention in an embodiment has a good performance in particular in the high-dimensional and low-sample size microarray data environment. Simulation studies and real data experiments further confirmed that the performance of this model outperforms other regularized methods such as those based on Lasso, SCAD and Elastic net. Thus, the Net-SVM model with $L_{1/2}$ regularization of embodiments of the present invention is highly advantageous as it allows selecting less but more effective genes in for example a complex protein-protein interaction network.

The system of the present invention may, thus, have a significant impact on diagnosis and treatment decisions for treating cancer, in particular it can be used for constructing a simple and satisfactory protein-protein interaction network for cancer diagnosis in a fast and accurate way.

Preferably but not exclusively, the system of the present invention can be used for classification, disease-related gene selection and finally construction of protein-protein interaction networks. The genes selected by the system can be seen as the molecular interaction information about the disease-related biological process, and then they can be gathered with the protein network information collected from some biological databases, such as BioGRID (Stark, Chris, et al., Nucleic acids research 34.suppl 1 (2006): D535-D539), which contains the biological interactions information from more than forty-three thousand publications. The constructed model which can combine the protein network information and molecular interaction information extracted from the biological process with analysis of the gene expression data has been proved for being biologically meaningful and can remove the noise effectively (Li, Caiyan, and Hongzhe Li., Bioinformatics 24.9 (2008): 1175-1182, Zhang, Wei, et al., PLoSComputBiol 9.3 (2013): e1002975).

Further features, applications and advantages of the system and method of the present invention will be evident for a person skilled in the art from the features and embodiments described below relating to the Net-SVM model with $L_{1/2}$ regularization of one embodiment of the present invention, and a coordinate descent method which can be used to complete the Net-SVM model with $L_{1/2}$ regularization.

A network $G=(V,E,W)$ is defined where V is the set of genes in the dataset and $e=(u\sim v)$ represents the set of edges which genes u and v are linked in the PPI network. W is the weight of the edges with $w(u,v)$ means the weight of the edge $e=(u\sim v)$. $d_v$ represents the degree of the gene u which is the number of the edges linked with u. The normalized Laplacian matrix L for W with the $u\sim v$ can be defined as (Chung, Fan RK. Spectral graph theory. Vol. 92. American Mathematical Soc., 1997):

$$L(u,v) = \begin{cases} 1 - \frac{w(u,v)}{d_u} & \text{if } u = v \text{ and } d_u \neq 0 \\ -\frac{w(u,v)}{\sqrt{d_u d_v}} & \text{if } u \text{ and } v \text{ are linked} \\ 0 & \text{otherwise} \end{cases} \quad (1)$$

This matrix L is always non-negative definite and many useful properties of the graph can be obtained in the corresponding set of the eigenvalues or spectrum.

Considering that the dataset contains n samples and p genes, with $$Y = (y_1, y_2, \ldots, y_n)^T$$

where $$y \in (0,1), X = (x_{i1}, x_{i2}, \ldots x_{ip})$$

indicate the p-dimension covariates. The support vector machine (SVM) model solves the following problem:

$$\min \sum_{i=1}^{n} \left[ 1 - y_i \left( \beta_0 + \sum_{j=i}^{p} \beta_j h_j(x_i) \right) \right] \quad (2)$$

where $\{h_1(x_1) \ldots h_p(x_p)\}$ are the dictionary of basic functions.

When adding the regularization part to the SVM model, it can be written as:

$$\min \sum_{i=1}^{n} \left[ 1 - y_i \left( \beta_0 + \sum_{j=i}^{p} \beta_j h_j(x_i) \right) \right] + \lambda \|\beta\|^q \quad (3)$$

where the $\lambda$ is the tuning parameter.

Following Suykens, Johan A K, and JoosVandewalle (Neural processing letters 9.3 (1999): 293-300), the Net-SVM proposed with the network constraint can be defined as:

$$f(\lambda_1, \lambda_2, \beta) = \quad (4)$$
$$\left\{ \min \sum_{i=1}^{n} \left[ 1 - y_i \left( \beta_0 + \sum_{j=i}^{p} \beta_j h_j(x_i) \right) \right] + \lambda_1 \|\beta\|^q \right\} + \lambda_2 \beta^T L \beta$$

where $\lambda_1$ and $\lambda_2$ are the tuning parameters. The first term is the log-likelihood function of the SVM model and the regularization part was used to induce a sparse solution. The second part is a network constraint based on the Laplacian matrix which was used to induce a smooth solution of the network.

According to Zou, Hui, and Trevor Hastie (Journal of the Royal Statistical Society: Series B (Statistical Methodology) 67.2 (2005): 301-320), a new set of $<X^*, Y^*>$ is suggested $$X^*_{(n+p)*p} = (1+\lambda_2)^{-1/2} \begin{pmatrix} X \\ \sqrt{\lambda_2} S^T \end{pmatrix}, Y^*_{(n+p)} = \begin{pmatrix} Y \\ 0 \end{pmatrix} \quad (5)$$

where $L = U \Gamma U^T$ and $S = U \Gamma^{1/2}$.

$$\star = \sqrt{1+\lambda_2}\,\beta \text{ and } \gamma = \frac{\lambda_1}{\sqrt{1+\lambda_2}}.$$

Let The formula (4) can also be written as:

$$f(\lambda_1,\lambda_2,\beta)=f(\gamma,\beta^*)=\min \Sigma_{i=1}^{n+p}[1-y_i^*(\beta_0^*+\Sigma_{j=1}^p \beta_j^* h_j(x_i^*))]+\gamma\Sigma_{j=1}^p|\beta_j^*|^q \quad (6)$$

Formula (6) can be used to solve the Net-SVM as an equivalent optimization problem with regularization. The $L_1$-type problem can be written as:

$$f(\gamma,\beta^*)=\min \Sigma_{i=1}^{n+p}[1-y_i^*(\beta_0^*+\Sigma_{j=1}^p \beta_j^* h_j(x_i^*))]+\gamma\Sigma_{j=1}^p|\beta_j^*|^1 \quad (7)$$

In general, the $L_1$-type regularization method can solve the optimization problem efficiently. However, when it is applied in the feature selection in biological data, because of the high-dimensional and low-sample size microarray data, the $L_1$-type regularization may produce many inconsistent gene selections and some results are the extra bias. In order to solve this problem, Xu et al. (Science China Information Sciences 53.6 (2010): 1159-1169) proposed the $L_{1/2}$ regularization method to obtain a more sparse solution. The inventors herein found based on their research and experiments that the sparsity, unbiasedness, and oracle properties of the $L_{1/2}$ regularization make it more suitable to be used for biological datasets. The Net-SVM model with the $L_{1/2}$ regularization can be written as:

$$f(\gamma,\beta^*) = \min \sum_{i=1}^{n+p}\left[1-y_i^*\left(\beta_0^* + \sum_{j=i}^{p}\beta_j^* h_j(x_i^*)\right)\right] + \gamma\sum_{j=1}^{p}|\beta_j^*|^{\frac{1}{2}} \quad (8)$$

$$= (Y^* - X^*\beta^*)^T(Y^* - X^*\beta^*) + \sum_{j=1}^{p}|\beta_j^*|^{\frac{1}{2}}$$

A coordinated descent method for the $L_{1/2}$ penalized Net-SVM model: the inventor herein discovered a coordinate descent method to implement the $L_{1/2}$ penalized Net-SVM model. The target function formula (8) can be optimized by respecting to the value of the coefficient $\beta_j$, the coordinated descent method will repeat for many cycles from j=1 to p iteratively until all the coefficients are converged. The coordinate descent method applied for $L_1$-type regularization by the soft thresholding operator can be defined as follows:

$$\beta(j) = \text{Soft}(\omega_j, \lambda) = \begin{cases} \omega_j + \lambda & \text{if } \omega_j < \lambda \\ \omega_j - \lambda & \text{if } \omega_j > \lambda \\ 0 & \text{if } |\omega_j| < \lambda \end{cases} \quad (9)$$

The new half threshold function was used to instead formula (9):

$$\beta(j) = \text{Half}(\omega_j, \lambda) = \quad (10)$$

$$\begin{cases} \frac{2}{3}\omega_j\left(1 + \cos\left(\frac{2(\pi - \varphi_\lambda(\omega_j))}{3}\right)\right) & \text{if } |\omega_j| > \frac{\sqrt[3]{54}}{4}(\lambda)^{2/3} \\ 0 & \text{otherwise} \end{cases}$$

where $\varphi_\lambda(\omega_j) = \arccos\left(\frac{\lambda}{8}\left(\left(\frac{|\omega_j|}{3}\right)^{-3/2}\right)\right).$ Based on the new half threshold function, the coordinate descent method designed with the Newton-Raphson iterative procedure for the $L_{1/2}$ penalized Net-SVM model can be given as follows:

Step 1: Initial all $\beta_j=0$ (j=1, 2 ... p) and $\gamma$; set m=0;
Step 2: Construct the Laplacian matrix L, the X* and Y*;
Step 3: Solve $$(Y^* - X^*\beta^*)^T(Y^* - X^*\beta^*) + \sum_{j=1}^{p}|\beta_j^*|^{\frac{1}{2}},$$

subject to the constraints of the Net-SVM model with penalties;
Step 4: Make m=m+1, update $\beta$=Half($\omega_j$, $\gamma$);
Step 5: Repeat Steps 3, 4 until all $\beta$(m) are converged.

Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein.

It will also be appreciated that where the methods and systems of the present invention are either wholly implemented by computing system or partly implemented by computing systems then any appropriate computing system architecture may be utilized. This will include standalone computers, network computers and dedicated hardware devices. Where the terms "computing system" and "computing device" are used, these terms are intended to cover any appropriate arrangement of computer hardware capable of implementing the function described.

It will be appreciated by persons skilled in the art that the term "database" may include any form of organized or unorganized data storage devices implemented in either software, hardware or a combination of both which are able to implement the function described.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

EXAMPLES

Example 1

Numerical Test, Simulation Experiment
To test the performance of the $L_{1/2}$ penalized Net-SVM model of the present invention, the results of the Net-SVM model was compared with four different regularizations: Elastic net, Lasso, SCAD and $L_{1/2}$ approaches. The test network datasets were generated as in (Li, Caiyan, and Hongzhe Li., Bioinformatics 24.9 (2008): 1175-1182):

Step 1: It is supposed that there are 200 independent transcription factors $x_n$, which each transcription factor regulates 10 different genes $x_m$, so that the constructed network contain about (200*10+200=2200) variables, set n=100. That means the dimension p=2200, and the size of the dataset n=100. The transcription factors $x_n$, $x_m$ are generated by the normal distribution N(0,1).

Step 2: Considering the correlation between the transcription factors and their respective regulated genes, the correlation coefficient was set r=0.75, the regulated genes $x_m$ will rewritten as: $x_m=(1-0.75)*x_m+0.75*x_n$. Combining the $x_m$ and $x_n$, total variable $X_i$ was obtained.

Step 3: Generating $$w = \left(5, \underbrace{\frac{5}{\sqrt{5}}, \ldots \frac{5}{\sqrt{5}}}_{10}, -5, \underbrace{\frac{-5}{\sqrt{5}}, \ldots \frac{-5}{\sqrt{5}}}_{10}, 3, \underbrace{\frac{3}{\sqrt{5}}, \ldots \frac{3}{\sqrt{5}}}_{10}, -3, \underbrace{\frac{-3}{\sqrt{5}}, \ldots \frac{-3}{\sqrt{5}}}_{10}, 0, \ldots 0\right)$$

and the noise control parameter $\varepsilon \sim N(0, \sigma_e^2)$.

Step 4: The corresponding $y_i$ was defined as:

$$\text{if } \frac{\exp(X_i w + \varepsilon)}{1 + \exp(X_i w + \varepsilon)} \geq 0.5, y_i = 1; \text{else } y_i = -1$$

The 10-fold cross validation (10-CV) approach was used in the experiments to tune the regularization parameters in the different penalized Net-SVM models. In order to get more accurate results, all methods in the different data environment will be evaluated for repeating 100 times.

Three parameters were used to compare the accuracy of the different methods in the test experiments, the percent correct, sensitivity and the specificity. The true positive (TP) was defined as the number of selected correct genes, false positive (FP) the number of the irrelevant genes which are selected, false negative (FN) the number of the related genes to the disease which are not selected, and the true negative (TN) the number of the irrelevant genes which are not selected by different methods.

$$\text{percent correct} = \frac{\text{selected correct genes}}{\text{total selected genes}}$$

$$\text{Sensitivity} = \frac{TP}{TP+FN}, \text{Specificity} = \frac{TN}{TN+FP}$$

Table 1 shows the performances of the Net-SVM models with different regularization methods. When comparing the number of selected correct genes, the Net-SVM with elastic net selected the most correct gene (43.82), the Net-SVM with $L_{1/2}$ selected the least (42.65), and nevertheless the gap of the results obtained by different methods is very small. For the number of the total selected genes, the Net-SVM with Lasso or with elastic net selected large numbers of genes. On the contrary, the Net-SVM model with the $L_{1/2}$ regularization only selected about 56.43 genes. The accuracy of gene selection with the $L_{1/2}$ regularization is higher (75.58%) than the results obtained with SCAD (61.15%), Lasso (13.23%) and elastic net (9.83%).

To compare the sensitivity, the values obtained by the methods are very close. In the specificity, the performance of Net-SVM with $L_{1/2}$ was the best. It means too many irrelevant genes were selected by other three methods. At last column of Table 1, the misclassification errors were shown. The Net-SVM model with elastic net achieved the largest misclassification error (8.12), the Net-SVM with the $L_{1/2}$ regularization achieved the least (4.59). It is evident that the Net-SVM model with $L_{1/2}$ regularization selects the lowest number of genes in the dataset and obtained the highest accuracy in gene selection, moreover, it has the best performance in the classification compared with other methods. Therefore it follows the Net-SVM model with $L_{1/2}$ regularization is an accurate and efficient method for high dimensional and low sample size biological datasets in cancer research.

TABLE 1

The gene selection performance of different Net-SVM models with different regularization methods

| methods | selected correct genes | total selected genes | percent correct | sensitivity | specificity | misclassification error |
|---|---|---|---|---|---|---|
| Net-SVM + $L_{1/2}$ | 42.65 | 56.43 | 75.58% | 96.93% | 99.36% | 4.59 |
| Net-SVM + SCAD | 42.83 | 70.04 | 61.15% | 97.34% | 98.74% | 5.03 |
| Net-SVM + Lasso | 43.31 | 327.28 | 13.23% | 98.43% | 86.83% | 7.74 |
| Net-SVM + Elastic net | 43.82 | 445.53 | 9.83% | 99.59% | 81.37% | 8.12 |

FIGS. 3 to 6 show the coefficient paths and misclassification errors obtained by the different methods in one run in the simulation experiments. The vertical dotted line was drawn at the optimal solution which is determined by the value of the minimal misclassification computed by the 10-fold cross validation. Accordingly, the solution path obtained by the Net-SVM model with the $L_{1/2}$ regularization is more sparse compared with other three methods.

Example 2

Real Data Experiment

In order to further evaluate the performances of the four Net-SVM methods with different penalty function, two real datasets were used:

The prostate tumour dataset: This dataset was used by Dinesh, S. et al. (Dinesh, Singh, et al., Cancer Cell 1.2 (2002):203-209) which contains about 12,600 genes and the number of the samples is 102 which contains 52 prostate tumour patients and another 50 are healthy. The prediction performance was evaluated of the four different Net-SVM methods using random partition: ¾ of the samples (the number is 77) were used as the training set and the other 25 samples were used for testing of the prediction capability.

The lung cancer dataset: The lung cancer dataset GDS3527 (Landi, Maria Teresa, et al., PloS one 3.2 (2008): e1651) which was download from NCBI's GEO Database (http://www.ncbi.nlm.nih.gov/sites/GDSbrowser). This lung cancer gene expression dataset contains of 22284 genes for 58 lung cancer patients and 49 healthy samples. 80 samples were used for the training and the other 27 samples were used for testing.

Tables 2-3 show the average results of the Net-SVM models with different penalty functions applied in two real datasets under 100 runs. In the results, the $L_{1/2}$ penalized Net-SVM model selected least genes, and meanwhile the elastic net approach selected most genes. The numbers of wrong classified patients of the four methods were very close and the performance of the method of the present invention proved to be the best. This is a very important factor in the clinical research, where the goal is trying to get an accurate result but using the least of genes in order to reduce the research costs.

TABLE 2

The results of the four Net-SVM models with different regularizations in prostate tumor dataset

| methods | selected genes | connected genes | connected edges | CV error | test error |
|---|---|---|---|---|---|
| Net-SVM + $L_{1/2}$ | 68.74 | 54.96 | 54.31 | 4.01/77 | 2.95/25 |
| Net-SVM + SCAD | 76.93 | 61.48 | 98.14 | 4.07/77 | 2.97/25 |
| Net-SVM + Lasso | 120.52 | 93.41 | 121.63 | 4.15/77 | 3.06/25 |
| Net-SVM + Elastic net | 215.17 | 182.62 | 176.86 | 4.21/77 | 3.07/25 |

TABLE 3

The results of the four Net-SVM models with different regularizations in lung cancer dataset

| methods | selected genes | connected genes | connected edges | CV error | test error |
|---|---|---|---|---|---|
| Net-SVM + $L_{1/2}$ | 180.32 | 76.57 | 80.15 | 6.56/80 | 3.88/27 |
| Net-SVM + SCAD | 214.56 | 102.11 | 111.48 | 6.76/80 | 3.92/27 |
| Net-SVM + Lasso | 306.19 | 178.26 | 239.34 | 7.02/80 | 4.16/27 |
| Net-SVM + Elastic net | 421.73 | 243.44 | 333.06 | 6.95/80 | 4.09/27 |

Below, a brief biological analysis of the results for the lung cancer dataset GDS3527 is given. In the FIGS. 7 to 10, the PPI networks related to the lung cancer obtained by four Net-SVM models with different penalty functions are given. It is obvious that the PPI network obtained by the $L_{1/2}$ penalized Net-SVM model is more concise than the other three networks; at the same time, as shown in Table 3, classification errors obtained by the method of the present invention are the lowest compared with other methods. Hence, the system and method of the present invention can help researchers construct the PPI network related to the disease fast and accurate.

Seen the four PPI networks constructed by the models, some important genes can be found in all four networks, such as RPA3, TAL1, MIF, SPP1, NME1, TTN, HSPB2, CRYAB, CAV1, ENO1 and so on, most of them are the center nodes in the PPI network which have a lot of split ends. However, an interesting problem can be seen. Although these genes are the important nodes to construct the PPI network, they may not be the decisive nodes to determine whether the person is the patient. Table 4 lists the 15 top-ranked disease-related genes which are selected by the four different regularization methods. The genes in bold were selected by all four models.

TABLE 4

The 15 top-ranked informative genes selected by Net-SVM models with different regularization methods

| Rank | $L_{1/2}$ | SCAD | Lasso | Elastic net |
|---|---|---|---|---|
| 1 | SPP1 | SPP1 | SPP1 | SPP1 |
| 2 | TEK | TAL1 | AGTR1 | AGTR1 |
| 3 | PECAM1 | AGTR1 | HK3 | CAT |
| 4 | TAL1 | HSPB2 | RASIP1 | HK3 |
| 5 | HIST1H2BJ | TEK | CD34 | TAL1 |
| 6 | AGTR1 | MIF | CAT | RASIP1 |
| 7 | RASIP1 | SASH1 | TAL1 | CD34 |
| 8 | CAV1 | CAV2 | FHL5 | TTN |
| 9 | EPAS1 | CAV1 | LDHA | FHL5 |
| 10 | SASH1 | NME1-NME2 | ARHGEF15 | LDHA |
| 11 | S1PR1 | CAT | TTN | ARHGEF15 |
| 12 | NME1 | ENO1 | CAV1 | VSIG4 |
| 13 | FHL1 | NUDT21 | SASH1 | GOLM1 |
| 14 | CAT | TTN | MIF | SASH1 |
| 15 | CRYAB | EPAS1 | NME1 | CAV1 |

In Table 4, only three center nodes can be found in the 15 top-ranked informative genes, SPP1, TAL1 and CAV1. These three genes were proved to be related to cancer: SPP1, the protein encoded by SPP1 is involved in the attachment of osteoclasts, and it was mentioned in Wu, Xin-Lin, et al. (World journal of gastroenterology: WJG 20.30 (2014): 10440) and Lin, Yiming, et al. (Inorganic phosphate induces cancer cell mediated angiogenesis dependent on forkhead box protein C2 (FOXC2) regulated osteopontin expression, Molecular carcinogenesis (2014)), which confirm that it is related to cancer. And the other genes, TAL1 and CAV1 were both said to play a role in cancer in the literature (Patel, B., et al., Leukemia 28.2 (2014):349-361, Loosveld, Marie, et al., Genes, Chromosomes and Cancer 53.1 (2014): 52-66, Sayhan, Sevil, et al., Ginekologiapolska 86.6 (2015): 424-428, Zhao, Zhi, et al., World journal of gastroenterology: WJG 21.4 (2015): 1140).

Besides these genes, there are also three genes which were selected by the four models, SASH1, AGTR1, and CAT. SASH1 plays an important role in tumor formation (Martini, Melanie, et al., The international journal of biochemistry & cell biology 43.11 (2011): 1630-1640). AGTR1 is an important effector to control blood pressure and volume in the cardiovascular system, and was found in the cancer pathway in the KEGG. CAT encodes the catalase which is an important antioxidant enzyme in the human body to defend against the oxidative stress. The oxidative stress plays an important role in the development of many chronic or late-onset diseases such as cancer, asthma and diabetes. It is obvious that this gene is associated with cancer (Shen, Yongchun, et al., Medicine 94.13 (2015): e679).

There are some other genes selected by the Net-SVM model with the $L_{1/2}$ regularization were not selected by other models. They were still related to the cancer. For example, the CRYAB, some studies pointed out that the high expression of CRYAB was correlated with poor survival in non-small cell lung cancer patients (Qin, Hui, et al., Medical Oncology 31.8 (2014): 1-8). Another gene NME1, this gene has been said to be related to cancer and plays a great role in inhibition of cancer in many studies. It is a very important gene in the cancer treatment (Banerjee, Shuvomoy, et al., Naunyn-Schmiedeberg's archives of pharmacology 388.2 (2014): 207-224, Niitsu, Nozomi, Journal of Clinical and Experimental Hematopathology 54.3 (2014): 171-177).

So, the genes only selected by $L_{1/2}$ penalized Net-SVM were also more related to the cancer. Above all, the present invention utilizing a Net-SVM model with $L_{1/2}$ regularization proved to be highly advantageous when identifying cancer-related genes accurately and efficiently.

The invention claimed is:

1. A method of determining an association of at least one biological feature with a medical condition, comprising the steps of:
obtaining a plurality of tissue samples, each of the plurality of tissue samples having a plurality of biological features,
obtaining a dataset comprising biological data related to the plurality of tissue samples;
applying at least some of the biological data to a regression model to determine and/or optimize parameters in the regression model thereby solving the regression model;
processing the biological data using the solved regression model with a biological model to determine one or more biological features that are associated with the medical condition,
wherein the biological model includes protein-protein interaction network information associated with the one or more biological features and the medical condition,
wherein the one or more biological features includes at least one of presence of a gene, gene expression, presence of a gene product, and amount of a gene product,
wherein the medical condition is cancer,
wherein the step of processing the biological data using the solved regression model with a biological model comprises the step of constructing a Laplacian matrix representing the dataset and/or the protein-protein interaction network information,
wherein the step of processing the biological data using the solved regression model with a biological model further comprises the step of introducing a network constraint to the regression model based on the Laplacian matrix,
wherein the step of processing the biological data using the solved regression model with a biological model includes an iterative transformation for obtaining at least one estimation representing correlation between the one or more biological features and the medical condition,
wherein the iterative transformation includes a soft thresholding operation of a coordinate descent optimization of the regularized protein-protein interaction network information for obtaining the regression model,
wherein a thresholding representation of $$\frac{\sqrt[3]{54}}{4}(\lambda)^{\frac{2}{3}}$$

is used in the soft thresholding operation, wherein $\lambda$ denotes a regularization parameter x.

2. The method in accordance with claim 1, wherein the regression model includes a support vector machine model with the network constraint.

3. The method in accordance with claim 1, wherein the regression model includes $L_{1/2}$ regularization.

4. The method in accordance with claim 1, further comprising the step of generating or obtaining the biological model for determining the association between the one or more biological features and the medical condition.

5. The method in accordance with claim 1, wherein the one or more biological features associated with the medical condition includes at least one biomarker and/or indicator arranged to represent an indication of the medical condition.

6. A system for determining an association of at least one biological feature with a medical condition, comprising a processing module arranged to:
apply at least some of the biological data in a dataset comprising biological data related to a plurality of samples each having a plurality of biological features to a regression model so as to determine and/or optimize parameters in the regression model thereby solving the regression model; and
process the biological data using the solved regression model with a biological model to determine one or more biological features that are associated with the medical condition,
wherein the biological model includes protein-protein interaction network information associated with the one or more biological features and the medical condition,
wherein the one or more biological features includes at least one of presence of a gene, gene expression, presence of a gene product, and amount of a gene product,
wherein the medical condition is cancer,
wherein the processing module is further arranged to construct a Laplacian matrix representing the dataset and/or the protein-protein interaction network information,
wherein the processing module is further arranged to introduce a network constraint to the regression model based on the Laplacian matrix,
wherein the processing module is further arranged to perform an iterative transformation for obtaining at least one estimation representing correlation between the one or more biological features and the medical condition
wherein the iterative transformation includes a soft thresholding operation of a coordinate descent optimization of the regularized protein-protein interaction network information for obtaining the regression model,
wherein a thresholding representation of $$\frac{\sqrt[3]{54}}{4}(\lambda)^{\frac{2}{3}}$$

is used in the soft thresholding operation, wherein $\lambda$ denotes a regularization parameter x.

7. The system in accordance with claim 6, wherein the regression model includes a support vector machine model with the network constraint.

8. The system in accordance with claim 6, wherein the regression model includes $L_{1/2}$ regularization.

9. The system in accordance with claim 6, wherein the biological model is generated by the processing module or is obtained from a database.

* * * * *